US008802055B2

United States Patent
Rajadurai et al.

(10) Patent No.: US 8,802,055 B2
(45) Date of Patent: Aug. 12, 2014

(54) USE OF THE SPIN CROSSOVER COMPLEX $[M^{x+}(L_y)H_w]AN)_z$ AS A MAGNETIC RESONANCE IMAGING CONTRAST AGENT

(75) Inventors: Chandrasekar Rajadurai, Madurai (IN); Mario Ruben, Strasbourg (FR); Danuta Kruk, Krakow (PL)

(73) Assignee: Karlsruher Institut fuer Technologie, Karlsruhe (DE)

( * ) Notice: Subject to any disclaimer, the term of this patent is extended or adjusted under 35 U.S.C. 154(b) by 700 days.

(21) Appl. No.: 12/810,084

(22) PCT Filed: Oct. 16, 2008

(86) PCT No.: PCT/EP2008/008749
§ 371 (c)(1),
(2), (4) Date: Sep. 8, 2010

(87) PCT Pub. No.: WO2009/080138
PCT Pub. Date: Jul. 2, 2009

(65) Prior Publication Data
US 2011/0002853 A1    Jan. 6, 2011

(30) Foreign Application Priority Data

Dec. 22, 2007 (EP) .................................. 07025065

(51) Int. Cl.
*A61K 49/06* (2006.01)
*A61K 49/00* (2006.01)
*A61K 31/4439* (2006.01)
*A61K 31/444* (2006.01)

(52) U.S. Cl.
CPC ............. *A61K 49/06* (2013.01); *A61K 31/4439* (2013.01); *A61K 31/444* (2013.01)
USPC ............................................ 424/9.1; 424/9.3

(58) Field of Classification Search
CPC .. A61K 31/4439; A61K 31/444; A61K 49/06
USPC ........................................................ 424/9.3
See application file for complete search history.

(56) References Cited

U.S. PATENT DOCUMENTS 5,858,329 A * 1/1999 Peng et al. ................ 424/9.361

OTHER PUBLICATIONS

Livramento et al. (Chem. Eur. J. 2006, 12, 989-1003).*
Costa et al. (J. Am. Chem. Soc. 2005, 127, 5147-5157).*

European Search Report for EP 07025065 dated Apr. 24, 2008.
International Search Report for PCT/EP2008/008749 mailed on Aug. 6, 2009.
Kruk et al., Field-dependent proton relaxation in aqueous solutions of some manganese(II) complexes: a new interpretation, Biol. Inorg. Chem., 8 (5), 512-518, 2003.
Kruk et al., Nuclear spin relaxation in paramagnetic systems with zero-field splitting and arbitrary electron spin, Phys. Chem. Chem. Phys., 3, 4907-4917, 2001.
Muller et al., Spin transition molecular materials: Intelligent contrast agents for magnetic resonance imaging, Journal of the American Chemical Society, Jul. 9, 2003 American Chemical Society, US—ISSN 0002-7863, vol. 125, Nr: 27, pp. 8405-8407, XP002478064, 2003.
Rajadurai et al., Above room temperature spin transition in a metallo-supramolecular coordination oligomer/polymer, Chemical Communications—Chemcom, May 1, 2007 Royal Society of Chemistry, GB—ISSN 1359-7345, vol. 25, pp. 2636-2638, XP002478130, 2007.
Rajadurai et al., Spin Transition in a Chainlike Supramolecular Iron(II) Complex, Inorganic Chemistry, Jan. 1, 2006 American Chemical Society, Easton, US—ISSN 0020-1669, vol. 45, Nr: 25, pp. 10019-10021, XP002472201, 2006.
Thompson et al., Structural studies of thermal- and light-induced transitions in iron(II) spin-crossover complexes, Comptes Rendus—Chimie, 20050901 Elsevier, Paris, FR—ISSN 1631-0748, vol. 8, Nr: 9-10, pp. 1365-1373, XP005096099, 2005.

* cited by examiner

*Primary Examiner* — Michael G Hartley
*Assistant Examiner* — Melissa Perreira
(74) *Attorney, Agent, or Firm* — Leydig, Voit & Mayer, Ltd.

(57) ABSTRACT

A method for magnetic resonance imaging of a human or animal body includes providing a spin crossover complex having the general formula $[M^{x+}(L_y)H_w]AN)_z$ wherein, $M^{x+}$ is a positively charged metal ion, $L_y$ is a heteroaromatic ligand containing at least one nitrogen atom in its ring system, AN is a negatively charged inorganic anion, w is 0, 1 or 2, x is 2 or 3, y is 2 or 3, and z is 2, 3 or 4.

The spin crossover complex is applied as a contrast agent in a magnetic resonance imaging of the human or animal body.

19 Claims, 1 Drawing Sheet

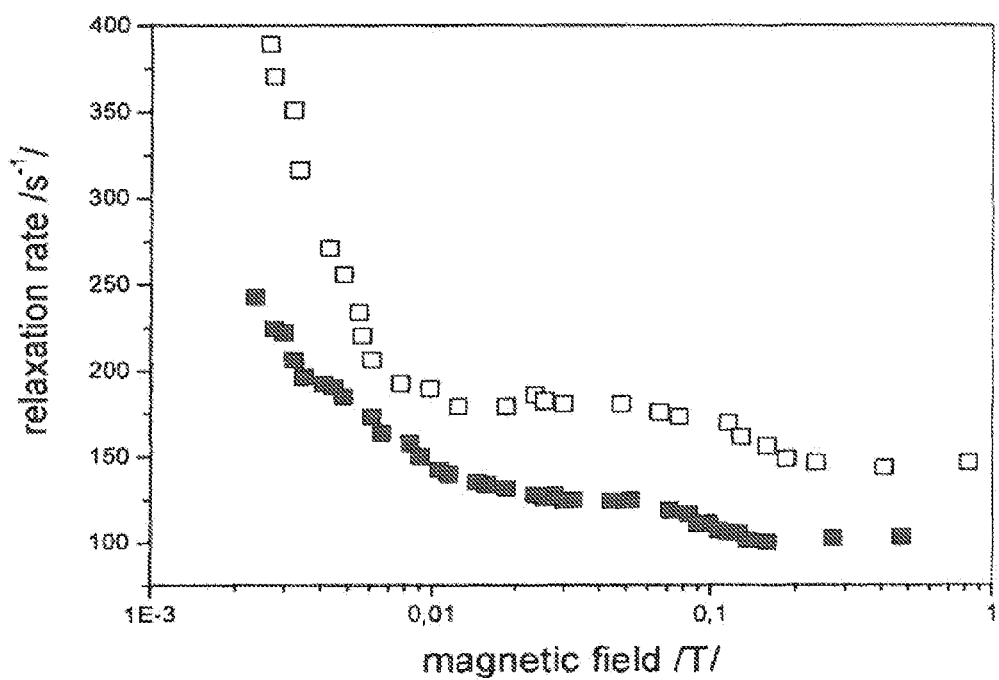
Proton spin-lattice relaxation rate ($R_1 = T_1^{-1}$) versus magnetic field (solid squares: 300K, open squares: 325K).

USE OF THE SPIN CROSSOVER COMPLEX [M$^{x+}$(L$_y$)H$_w$]AN)$_z$ AS A MAGNETIC RESONANCE IMAGING CONTRAST AGENT

CROSS REFERENCE TO PRIOR APPLICATIONS

This application is a U.S National Phase application under 35 U.S.C. §371 of International Application No. PCT/EP2008/008749, filed on Oct. 16, 2008 and which claims benefit to European Patent Application No. 07025065.9, filed on Dec. 22, 2007. The International Application was published in English on Jul. 2, 2009 as WO 2009/080138 A2 under PCT Article 21(2).

FIELD

The present invention relates to contrast agents for magnetic resonance imaging (MRI).

BACKGROUND

An active field of application of nuclear relaxation enhancement is the development and use of magnetic materials as contrast agents in magnetic resonance imaging. The magnetic species enhance the proton relaxation rates due to a random variation of the electron spin—nuclear spin interactions (the dipole-dipole interaction and the magnetic hyperfine interaction between the nuclear and electron magnetic moments), which open new pathways for longitudinal as well as transverse relaxation.

A category of contrast agents is paramagnetic solutions of transition metal complexes (such as Gd and Mn based contrast agents). In this case, the origin of the nuclear relaxation enhancement is found in the value of the electronic magnetic moment (about 650 times that of the proton). The efficiency of contrast agents is investigated involving a concept of relaxivity, referring to the nuclear relaxation enhancement normalized to 1 mM concentration of the magnetic species. At not too high concentration of the paramagnetic species, the enhancement is proportional to that concentration. Measurements of the relaxation enhancement or relaxivity over a broad range of magnetic fields are referred to as relaxometry, and the resulting curve is denoted as a nuclear magnetic relaxation dispersion (NMRD) profile. On the experimental side, the NMRD profiles are usually measured by the field-cycling technique, where the magnetic field is rapidly switched between different values. The measured relaxivity values for Gd and Mn based contrast agents are usually in the range of 20-50 1/mM*s. See (D. Kruk, T. Nilsson, J. Kowalewski, Phys. Chem. Chem. Phys., 3, 4907-4917, (2001), D. Kruk, J. Kowalewski, J. Biol. Inorg. Chem., 8 (5), 512-518, (2003)).

The publication Chandrasekar Rajadurai, Frank Schramm, Susan Brink, Olaf Fuhr, Robert Kruk, Mohammed Ghafari, Mario Ruben, "Spin Transition in a Chainlike Supramolecular Iron(II) Complex", Inorg. Chem. (communication), (2006), 45, 10019-10021 describes the synthesis, structure and characterization of the spin transfer complex [Fe$^{II}$-(L)$_2$H](ClO$_4$)$_3$.MeOH [L=4'-(4'''-pyridyl)-1,2':6'1''-bis-(pyrazolyl) pyridine] (complex 1). The publication also describes the reversible, thermally driven spin transition at 286 K with a hysteresis loop of ca. 2 K of complex 1.

The publication of Chandrasekar Rajadurai, Olaf Fuhr, Robert Kruk, Mohammed Ghafari, Horst Hahn and Mario Ruben, "Above room temperature spin transition in a metallo-supramolecular coordination oligomer/polymer", Chem. Commun., 2007, 2636-2638 describes the spin transition and other physical properties of the complex 1.

SUMMARY

An aspect of the present invention is to provide agents which can be used as a contrast agent in magnetic resonance imaging. A further, alternative aspect of the present invention is to provide an advantageous use of the above mentioned spin crossover complexes.

In an embodiment, the present invention provides for magnetic resonance imaging of a human or animal body which includes providing a spin crossover complex having the general formula [M$^{X+}$(L$_y$)H$_w$]AN)$_z$
wherein,
M$^{X+}$ is a positively charged metal ion,
L$_y$ is a heteroaromatic ligand containing at least one nitrogen atom in its ring system,
AN is a negatively charged inorganic anion,
w is 0, 1 or 2,
x is 2 or 3,
y is 2 or 3, and
z is 2, 3 or 4.
The spin crossover complex is applied as a contrast agent in a magnetic resonance imaging of the human or animal body.

BRIEF DESCRIPTION OF THE DRAWING

The present invention is described in greater detail below on the basis of embodiments and of the drawings in which:

FIG. 1 shows the proton spin-lattice relaxtion rate (R$_1$=T$_1$$^{-1}$) versus magnetic field.

DETAILED DESCRIPTION

Complexes with the general formula [M$^{X+}$(L$_y$)H$_w$]AN)$_z$ can, for example, have Fe$^{2+}$ or Fe$^{3+}$ or Co$^{2+}$ for the metal ion M$^{X+}$. Complexes having the general formula [M$^{X+}$(L$_y$)H$_w$]AN)$_z$ can, for example, have BF$_4$$^-$ or Cl$^-$ or SO$_4$$^{2-}$ or ClO$_4$$^-$ for the inorganic anion AN and/or with L =(4'-(4'''-pyridyl)-1,2':6'1''-bispyrazolylpyridine) and y=2.

In an embodiment of the present invention, complexes have the following structure:

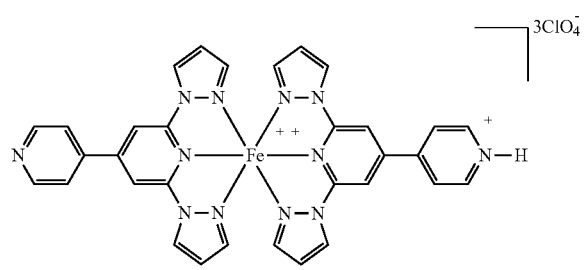

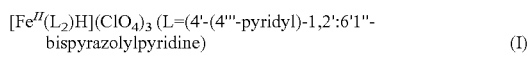

[Fe$^{II}$(L$_2$)H](ClO$_4$)$_3$ (L=(4'-(4'''-pyridyl)-1,2':6'1''-bispyrazolylpyridine)        (I)

The complexes according to the present invention are applied in the usual way as contrast agents, for example, orally or intravenously. Poisonous anions are not used.

The present invention is hereinafter explained in greater detail:

The above mentioned Iron(II) containing spin crossover complex [Fe$^{II}$(L$_2$)H$_w$](ClO$_4$)$_3$.MeOH (I) (w=1) was used to test the NMRD relaxation profile of the compound with different magnetic field. In this experiment, the NMRD relaxation profiles of the compound were collected for the discussed material.

The diagram according to FIG. 1 was obtained.

One can conclude from this experiment that:
1. The proton relaxation is very efficient (taking into account comparable distances between the electron spin and proton spin in this case and in the case of the mentioned paramagnetic contrast agents).
2. A significant difference between the proton relaxation rates in a guide narrow temperature range is observed. This effect can be due to the thermally driven spin transition of Fe. There is a mixture of HS (high spin) and LS (low spin) states of Fe at 300K. The relaxation enhancement can be caused by the presence of the magnetic moment associated with HS Fe. Upon heating, the HS fraction has further increased leading to a more efficient proton relaxation. The relaxation enhancement is very sensitive for the fraction of HS Fe.
3. Better relaxation rates were found at higher temperatures (see the open squares of FIG. 1), which are useful to discriminate warmer regions of the human or animal bodies, such as tumor tissue.

The present invention is not limited to embodiments described herein; reference should be had to the appended claims.

The invention claimed is:

1. A method for magnetic resonance imaging of a human or animal body, the method comprising:
introducing into the human or animal body a contrast agent comprising a spin crossover complex of formula

[M(L$_y$)H$_w$](AN)$_z$ wherein,
M is $Fe^{2+}$, $Fe^{3+}$, or $Co^{2+}$,
L is 4'-(4'''-pyridyl)-1,2':6'1''-bispyrazolylpyridine,
AN is a negatively charged inorganic anion,
w is 0, 1, or 2,
y is 2 or 3, and
z is 2, 3, or 4; and
conducting magnetic resonance imaging on the human or animal body.

2. The method as recited in claim 1, wherein M is $Fe^{2+}$.

3. The method as recited in claim 1, wherein AN is $BF_4^-$, $Cl^-$, $SO_4^{2-}$, or $ClO_4^-$.

4. The method as recited in claim 1, wherein y is 2.

5. The method as recited in claim 1, wherein M is $Fe^{3+}$.

6. The method as recited claim 1, wherein M is $Co^{2+}$.

7. The method as recited in claim 2, wherein AN is $BF_4^-$.

8. The method as recited in claim 2, wherein AN is $Cl^-$.

9. The method as recited in claim 2, wherein AN is $SO_4^{2-}$.

10. The method as recited in claim 5, wherein AN is $ClO_4^-$.

11. The method as recited in claim 5, wherein AN is $BF_4^-$, $SO_4^{2-}$, or $Cl^-$.

12. The method as recited in claim 5, wherein AN is $ClO_4^-$.

13. The method as recited in claim 6, wherein AN is $BF_4^-$, $SO_4^{2-}$, or $Cl^-$, or $ClO_4^-$.

14. The method as recited in claim 1, wherein the contrast agent consists essentially of the spin crossover complex, and AN is $BF_4^-$, $SO_4^{2-}$, $Cl^-$, or $ClO_{4-}$.

15. The method as recited in claim 4, wherein M is $Fe^{2+}$.

16. The method as recited in claim 1, wherein the spin crossover complex has a formula:

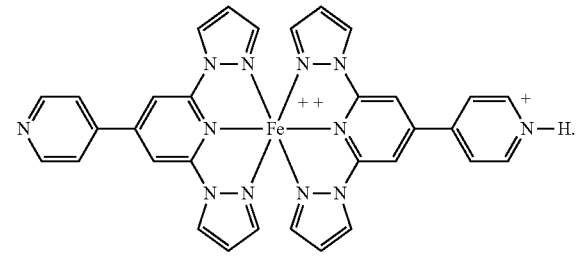

17. The method as recited in claim 1, wherein the introducing is intravenous.

18. The method as recited in claim 1, wherein y is 3.

19. The method as recited in claim 4, wherein AN is $BF_4^-$, $Cl^-$, $SO_4^{2-}$, or $ClO_4^{31}$.

* * * * *